Figure 3:
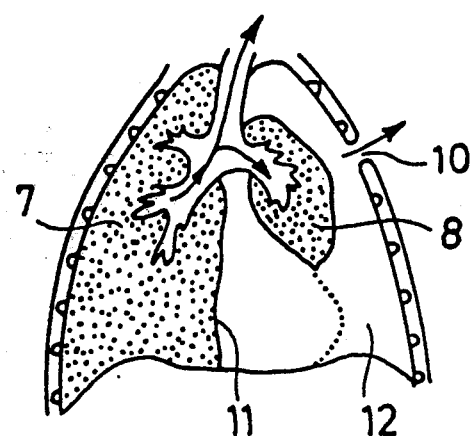

United States Patent [19]

Pollitt

[11] Patent Number: 5,195,977
[45] Date of Patent: Mar. 23, 1993

[54] VALVE PLASTER FOR THE EMERGENCY TREATMENT OF OPEN THORAX INJURIES

[75] Inventor: Sebastian Pollitt, Rheinbrohl, Fed. Rep. of Germany

[73] Assignee: Lohmann GmbH & Co. KG, Neuwied, Fed. Rep. of Germany

[21] Appl. No.: 709,933

[22] Filed: Jun. 4, 1991

[30] Foreign Application Priority Data

Jun. 9, 1990 [DE] Fed. Rep. of Germany ....... 4018591

[51] Int. Cl.$^5$ .............................................. A61M 1/00
[52] U.S. Cl. .................................... 604/122; 128/888
[58] Field of Search ................ 604/122, 126, 247; 128/888, 889

[56] References Cited

U.S. PATENT DOCUMENTS

| | | | |
|---|---|---|---|
| 1,920,808 | 8/1933 | Sander | 128/888 |
| 3,419,006 | 12/1968 | King . | |
| 4,399,816 | 8/1983 | Spangler | 128/888 |
| 4,465,062 | 8/1984 | Versaggi et al. | 604/122 |
| 4,717,382 | 1/1988 | Clemens et al. | 604/122 |
| 4,813,941 | 3/1989 | Shea . | |

*Primary Examiner*—Paul J. Hirsch
*Attorney, Agent, or Firm*—Sprung Horn Kramer & Woods

[57] ABSTRACT

A plaster which comprises a gas check valve being inserted in an aperture and which, on the side facing the skin, is provided with a carrier being coated with a pressure sensitive adhesive, makes the emergency treatment of open thorax injuries possible.

8 Claims, 2 Drawing Sheets

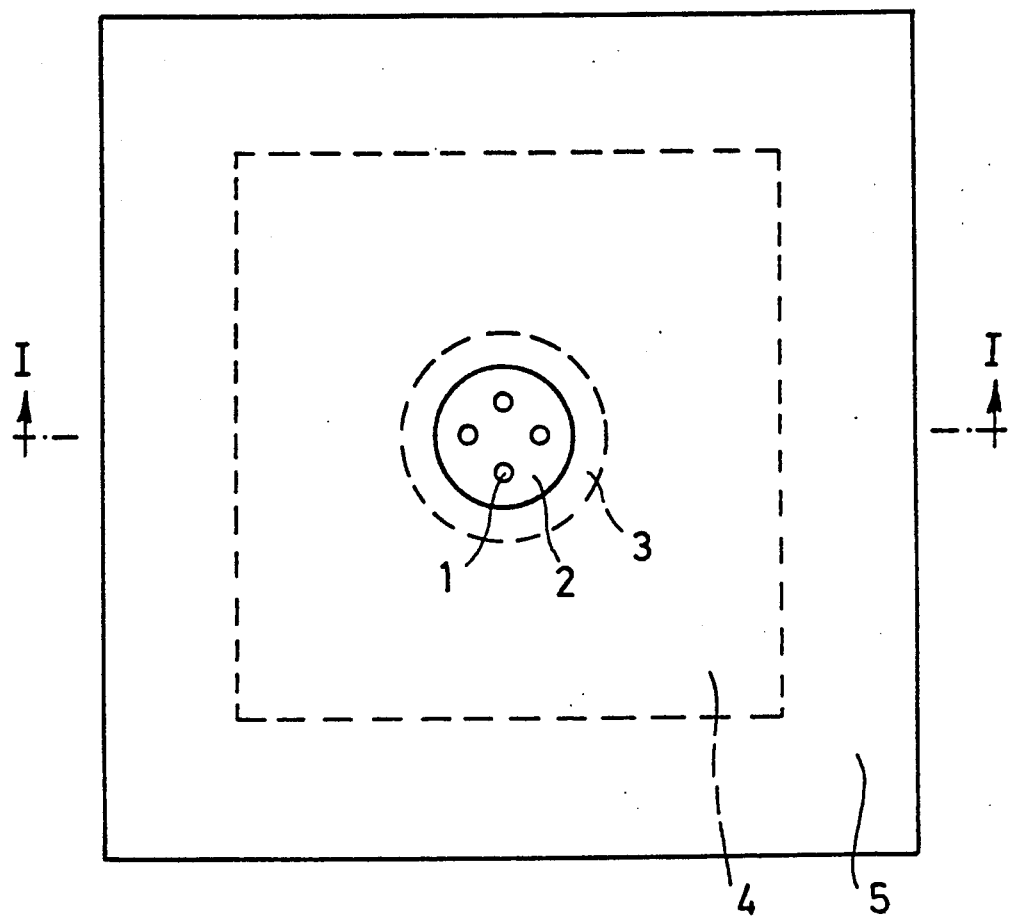
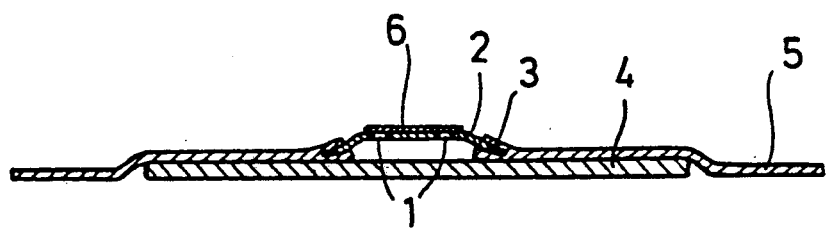
FIG.2

VALVE PLASTER FOR THE EMERGENCY TREATMENT OF OPEN THORAX INJURIES

DESCRIPTION

The present invention relates to a plaster for emergency treatment of open thorax injuries.

In addition to the high risk of infections, injuries passing through the chest are extremely critical because they may immediately result in an extreme slowing of the respiration. One reason therefor is the fact that the negative pressure normally prevailing within the thorax (approximately 4 to 8 mm Hg) breaks down, since due to the injury a pressure compensation with the environment takes place causing the lobe of the lung on the injured side to deflate.

Another impairment of the thoracic respiration of the pulmonary lobe on the uninjured side arises due to the fact that the mediastinum located between the two lobes of the lung is laterally displaced towards the uninjured side because of the resulting pressure conditions. Thus, in addition to the failure of one pulmonary lobe, respiration is restrained due to a reduced respiratory volume of the lung lobe on the uninjured side.

In addition, the so-called lesser circulation is stressed so much that an overstrain may result and this means another serious danger to the life of the injured person.

Relative to the total number of accidents, thorax injuries amount to 9%. Considering this fact and taking into account that the death rate within the first, approximately 6 hours after the respective accident is very high, one can easily realize the severe problem, both with respect to quality and to quantity.

Several suggestions for the first-aid treatment of such sucking wounds have been made, however, as a whole they do not deliver satisfactory results. An example of these proposals is the so-called imbricated bandage, i.e., a compression bandage, where adhesive strips are placed on top of each other in a tile-shaped manner around approximately three quarters of the thorax so that the injury can be closed provisionally. Other forms of pressure bandages have also been proposed.

In cases where there is no bandaging material available, it has been proposed to lay the palm on the injury. Another proposal for extreme situations is to pull lung tissue of the injured side into the gap of the wound in order to close the wound provisionally. Except for the fact that this is a questionable treatment, it can obviously only be performed by a physician.

Another alternative for emergency bandaging is the "Device for emergency bandaging of an open thorax injury" according to DE 36 31 650 A1. This device is characterized by a substantially cup-shaped hollow body of a gas-tight material having a free edge being formed as an elastic, soft sealing ring which is to be located at the outer side of the thorax and which, when applied, surrounds the thorax injury at a distance; said free edge being provided with a ventilation device by means of which the interior space of said ring can be aerated under formation of negative pressure within the interior space of the hollow body.

All of the known measures without accessories at best prevent further passage of air through the wound but do not improve respiration. In addition, the person rendering the first aid is impeded in carrying out additional, probably vital measures.

When a hand is laid or pressed on the wound, the injured person who already suffers from heavy breathing in addition may be seized with anxiety. The disadvantage of the device according to DE 36 31 650 A1 is the fact that it is too expensive and too complicated for a person without medical training, i.e., is difficult to handle (cf. Medizingeräteverordnung [regulation on medical appliances] of Jan. 14, 1985, §§ 2 and 6, paragraph 3 and 4).

The object of the present invention is to provide a device suitable and destined, in particular for a first-aid measure rendered within the limits of emergency treatment until clinical care. Said device shall permit external closure of the wound gap and rapidly and permanently improve the respiration of the injured person to a considerable extent.

This object is achieved by providing a plaster with a gas check valve responding to even slight pressure variations. This valve closes during the inspiration phase, in which a negative pressure is built up within the thorax, so that no additional air may enter the chest, whereas it opens during the expiration phase in which positive pressure is formed by lowering the ribs and lifting the diaphragm so that the air which already entered the pleural cavity may escape through the valve.

This enables the lobe of the lung to gradually deploy again after each expiration until—in the most favorable case—it achieves its full function. According to an advantageous embodiment of the present invention, the plaster may additionally be provided with a wound dressing and rendered sterile; in this case bandaging of the injury under nearly aseptic conditions is ensured at the same time. Effective treatment in case of larger injuries or those which are difficult to localize can be effected by different sizes of the dressings.

The plaster is provided with a carrier layer preferably being substantially air-tight. Said carrier layer may be a textile fabric, such as a woven, non-woven, or a film, e.g., a plastic film or a metal foil. The carrier layer has a pressure-sensitive adhesive coating. In this connection the pressure sensitive adhesive may be a natural one, e.g., a rubber adhesive, or a technical one, such as an acrylic adhesive. The carrier layer exhibits an aperture to accommodate the gas check valve which may be a diaphragm, ball, plug, or a spring-type valve. It responds to even slight pressure variations and operates reliably. On the bottom side of the carrier layer there is a wound dressing consisting of textile material. It may have a multi-layer structure. The material is permeable to air and highly absorptive; its surface is designed in such a way that it does not stick to the wound. The latter may be achieved by aluminizing.

The plaster is applied to a protective layer which is removed prior to application. The plaster is preferably aseptically packed in a suitable package (e.g. in a peelable bag).

The present invention provides a simple and safe first-aid treatment of an open thorax injury. The plaster may be used in any situation without delay and even an untrained layman can apply it. After application of this plaster the person rendering the first aid has his hands free to perform further, probably vital first-aid measures. The plaster does neither burden nor restrict the injured person as would be the case, e.g., when the hand is pressed on the chest, so that an anxiety condition due to such a treatment will not occur.

The figures represent an embodiment example of the present invention; they are described in more detail in the following:

FIG. 1: represents a plan view on the plaster with a diaphragm valve after removal of the membrane.

FIG. 2: shows a cross-section along line I/I of FIG. 1 of the valve plaster with applied membrane.

FIG. 3: is a schematic representation of the thorax with an open injury during expiration.

Figure 4:
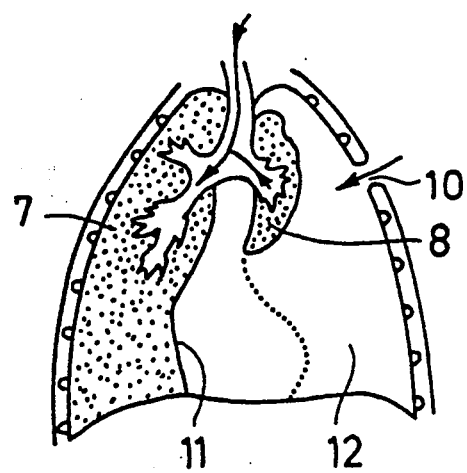

FIG. 4: is the representation according to FIG. 3 during inspiration.

Figure 5:
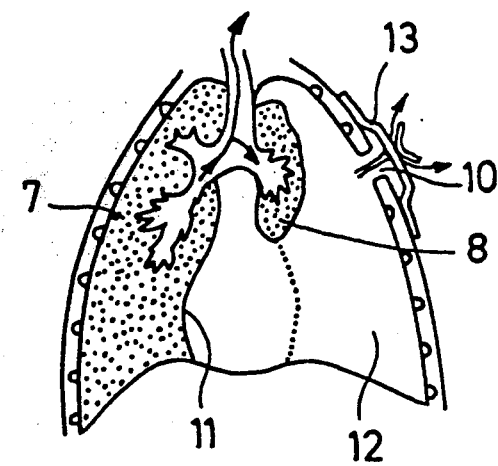

FIG. 5: is a representation according to FIG. 3 with the plaster according to FIG. 1 applied during expiration.

Figure 6:
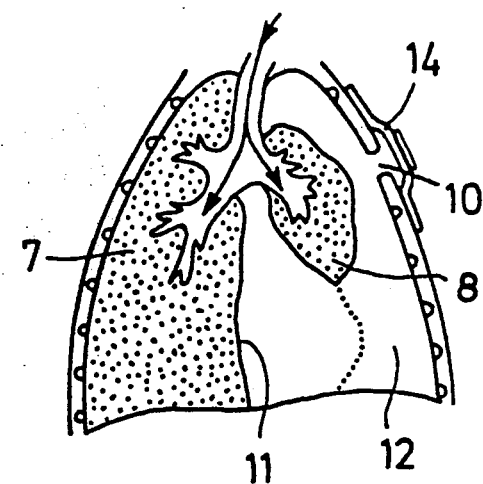

FIG. 6: is a representation according to FIG. 5 during inspiration.

FIG. 1 represents in plan view an embodiment example of the valve plaster for first-aid measures of open thorax injuries; FIG. 2 is a cross-section along line I/I. The plaster has a diaphragm valve 2 positioned in the middle of the carrier material 5. The diaphragm valve 2 consists of a plastic disc with four holes 1 having a diameter of 4 mm; they are covered by a membrane (shown in FIG. 2) being glued thereon. The membrane 6 is capable of closing the holes 1 hermetically.

From the bottom side of the carrier material 5 a ring 3 consisting of the same material as the carrier material 5 is glued in order to improve fixation of the diaphragm valve 2; the ring 3 partly sticks on the diaphragm valve 2 and partly on the carrier material 5.

The schematic drawing of FIG. 3 shows a sectional view on a part of a chest with thorax injury 10. It can be recognized that the lobe of the lung 8 on the injured side already collapsed to a large extent since the pressure within the respective thoracic cavity 12 has undergone a pressure compensation with the environment; the other pulmonary lobe 7 is in a substantially normal position during expiration shown in FIG. 3, since the mediastinum 11 is also in almost central and thus normal position.

During inspiration according to FIG. 4, the mediastinum is displaced towards the pulmonary lobe 7 whereby the lobe 8 continues to collapse.

If a plaster 13 according to the present invention is applied on the outer side of the thorax (FIG. 5) in such a way that the wound dressing 4 is lying above the injury 10, a slight positive pressure within the interior 12 of the thorax is formed during expiration. As a result the valve 6 opens and the air flows out through holes 1.

If the plaster 14 according to the present invention is applied as shown in FIG. 6, negative pressure within the thoracic cavity is formed during inspiration; the valve closes and the collapsed lobe 8 can slightly recover due to the negative pressure.

Each breath thus improves the state of the injured person.

It is understood that the specification and examples are illustrative but not limitative of the present invention and that other embodiments within the spirit and scope of the invention will suggest themselves to those skilled in the art.

I claim:

1. A plaster for the emergency treatment of open thorax injuries permitting external closure of the wound gap and improving the respiration of the injured person until clinical treatment, comprising a wound dressing (4), a substantially airtight carrier layer (5) provided with a pressure-sensitive adhesive coating on the side which will face the skin, the carrier layer (5) projecting beyond the lateral edges of the wound dressing and being provided with an aperture, a gas check valve (2) responding to slight pressure variations projecting through the aperture, the gas check valve opening when positive pressure builds up during the expiration phase and permitting air to escape from the chest cavity, and closing when negative pressure arises during the inspiration phase, the plaster being relatively flat and of low profile.

2. The plaster according to claim 1, wherein the gas check valve (2) is a diaphragm valve.

3. The plaster according to claim 1, wherein the gas check valve (2) is positioned on the side of the carrier layer (5) remote from the skin, the plaster further including a ring (3) having a protruding profile and an inner protruding edge and an outer bottom edge, the ring being of the same material as the carrier and being positioned on the carrier layer for fixation of said gas check valve, one surface portion of the inner protruding edge of said ring (3) sticking to the diaphragm forming the gas check valve (92) and one surface portion of its outer bottom edge sticking to the carrier layer (5).

4. The plaster according to claim 1, wherein the wound dressing (4) comprises a material permeable to air and highly absorptive, said wound dressing having a surface which prevents the wound dressing from sticking to the wound (10).

5. The plaster according to claim 4, wherein the dressing surface is aluminized to prevent sticking.

6. The plaster according to claim 1, wherein the carrier comprises a textile fabric.

7. The plaster according to claim 1, wherein the carrier comprises a film.

8. The plaster according to claim 1, wherein the wound dressing comprises multiple layers.

* * * * *